United States Patent
Knutsson

(10) Patent No.: US 9,733,474 B2
(45) Date of Patent: Aug. 15, 2017

(54) REFERENCE CALIBRATION FOR AN ADAPTIVE OPTICS SYSTEM

(71) Applicants: Zoran Popovic, Molndal (SE); Jorgen Thaung, Molndal (SE); Mette Owner-Petersen, Molndal (SE); Bengt Svensson, Molndal (SE); Per Knutsson, Molndal (SE)

(72) Inventor: Per Knutsson, Molndal (SE)

(73) Assignee: Zoran Popovic, Jörgen Thaung, Mette Pedersen-Owner, Bengt Svensson and Per Knutsson, Mölndal (SE)

( * ) Notice: Subject to any disclaimer, the term of this patent is extended or adjusted under 35 U.S.C. 154(b) by 0 days.

(21) Appl. No.: 15/142,238

(22) Filed: Apr. 29, 2016

(65) Prior Publication Data
US 2016/0246053 A1 Aug. 25, 2016

Related U.S. Application Data

(63) Continuation of application No. 14/349,093, filed on Apr. 2, 2014, now Pat. No. 9,335,603.

(30) Foreign Application Priority Data

Oct. 7, 2011 (EP) .................................. 11184413

(51) Int. Cl.
*G02B 26/00* (2006.01)
*G02B 27/00* (2006.01)
(Continued)

(52) U.S. Cl.
CPC ........ *G02B 27/0068* (2013.01); *A61B 3/0025* (2013.01); *A61B 3/1015* (2013.01);
(Continued)

(58) Field of Classification Search
USPC .................................................. 359/290–295
See application file for complete search history.

(56) References Cited

U.S. PATENT DOCUMENTS

| 8,248,684 B2 | 8/2012 | Robinson et al. |
| 2004/0156015 A1* | 8/2004 | Campbell .............. A61B 3/103 351/205 |

(Continued)

FOREIGN PATENT DOCUMENTS

WO    03027749 A    4/2003

OTHER PUBLICATIONS

International Search Report mailed Oct. 23, 2012, for International Application PCT/EP2012/069620, 4 pages.

(Continued)

*Primary Examiner* — Mohammed Hasan
(74) *Attorney, Agent, or Firm* — Remarck Law Group PLC

(57) ABSTRACT

A method of determining a reference calibration setting for an adaptive optics system (1) comprising a detecting device (8) for detecting light from an object (5); and at least one controllable wavefront modifying device (9) arranged such that light from the object (5) passes via the wavefront modifying device (9) to the detecting device (8). The method comprises the steps of: arranging (100) a light-source between the object (5) and the wavefront modifying device (9) to provide a reference light beam to the detecting device (8) via the wavefront modifying device; for each of a plurality of orthogonal wavefront modes of the wavefront modifying device: controlling (101) the wavefront modifying device to vary a magnitude of the orthogonal wavefront mode over a predetermined number of magnitude settings; acquiring (102) a series of readings of the detecting device, each reading corresponding to one of the magnitude settings; determining (103) a quality metric value indicative of an
(Continued)

information content of the reading for each reading in the series of readings, resulting in a series of quality metric values; and determining (106) a reference parameter set for the wavefront modifying device corresponding to an optimum quality metric value based on the series of quality metric values.

10 Claims, 2 Drawing Sheets

(51) Int. Cl.
*F41H 13/00* (2006.01)
*G01J 9/02* (2006.01)
*A61B 3/14* (2006.01)
*G02F 1/19* (2006.01)
*A61B 3/00* (2006.01)
*A61B 3/10* (2006.01)
*G01J 9/00* (2006.01)
*G06T 5/10* (2006.01)
*H04N 5/225* (2006.01)
*G02B 26/06* (2006.01)

(52) U.S. Cl.
CPC ............. *A61B 3/14* (2013.01); *F41H 13/005* (2013.01); *G01J 9/00* (2013.01); *G01J 9/02* (2013.01); *G02F 1/19* (2013.01); *G06T 5/10* (2013.01); *H04N 5/2256* (2013.01); *G02B 26/06* (2013.01); *G06T 2207/20048* (2013.01)

(56) References Cited

U.S. PATENT DOCUMENTS

2008/0259273 A1 10/2008 Williams et al.
2010/0245976 A1 9/2010 George et al.
2016/0062112 A1\* 3/2016 Potsaid ............... G02B 26/105
356/497

OTHER PUBLICATIONS

Liang, J. et al., "Objective measurement of wave aberrations of the human eye with the use of a Hartmann-Shack wave-front sensor," Journal of the Optical Society of America, American Institute of Physics, New York, vol. 11, No. 7, Jul. 1994, pp. 1949-1957.

\* cited by examiner

US 9,733,474 B2

REFERENCE CALIBRATION FOR AN ADAPTIVE OPTICS SYSTEM

CROSS-REFERENCE TO RELATED APPLICATIONS

This application is a Continuation of U.S. application Ser. No. 14/349,093 filed Apr. 2, 2014 now U.S. Pat. No. 9,335,603 B2, which is a 371 U.S. National Stage of International Application No. PCT/EP2012/069620, filed Oct. 4, 2012, which claims priority to EP Application No. 11184413.0, filed Oct. 7, 2011. The disclosure of each of the above applications is incorporated herein by reference in their entirety.

TECHNICAL FIELD OF THE INVENTION

The present invention relates to a method of determining a reference calibration setting for an adaptive optics system comprising a detecting device for detecting light from an object, and at least one controllable wavefront modifying device arranged such that light from said object passes via said wavefront modifying device to said detecting device. The present invention also relates to such an adaptive optics system.

TECHNICAL BACKGROUND

Adaptive optics has been applied in different areas of science and industry, e.g. to enhance the capabilities of imaging systems in astronomy, microscopy, and ophthalmology, to enhance signal quality in optical communication systems, and also in laser beam control. In environments where an imaging system is used to observe objects behind a continuously evolving phase curtain (atmosphere, ocular optics, heating effects, etc.), the adaptive optics system can effectively mitigate the effects of this medium to regain the loss of imaging performance.

The purpose of an adaptive optics system is to correct aberrations, or phase errors, thereby reducing the phase variance. However, in many adaptive optics systems, the wavefront sensor is relative (e.g. a Shack-Hartmann sensor), meaning that static errors are unseen if not calibrated correctly. Even with an absolute wavefront sensor, non-common path errors specific to the detecting path imply an aberrated imaging/detecting channel. It is therefore crucial to reduce these effects to achieve optimal performance of the adaptive optics system.

One way of achieving a reference calibration for a wavefront sensor would be to provide a reference plane wave and to register the output of the wavefront sensor in response to that reference plane wave. It, however, appears difficult and costly to achieve such a perfect plane wave.

U.S. Pat. No. 6,609,794 discloses an alternative method for reference calibration of an adaptive optics system using a modified Shack-Hartmann sensor as a wavefront sensor. According to U.S. Pat. No. 6,609,794, each lenslet in the lenslet array comprised in the Shack-Hartmann sensor is provided with a substantially opaque element in the center of the lenslet. By illuminating the thus modified Shack-Hartmann sensor with a reference beam, a reference or zero-point reading can be acquired.

Although the approach of U.S. Pat. No. 6,609,794 seems to represent a simplified way of achieving a reference calibration of a wavefront sensor, there is still room for improvement. For example, a special kind of wavefront sensor is required and aberrations in the detecting path are not taken into account.

SUMMARY OF THE INVENTION

In view of the above-mentioned and other drawbacks of the prior art, a general object of the present invention is to provide for an improved reference calibration of an adaptive optics system.

According to a first aspect of the present invention, these and other objects are achieved through a method of determining a reference calibration setting for an adaptive optics system comprising: a detecting device for detecting light from an object; and at least one controllable wavefront modifying device arranged such that light from the object passes via the wavefront modifying device to the detecting device, the method comprising the steps of: arranging a light-source between the object and the wavefront modifying device to provide a reference light beam to the detecting device via the wavefront modifying device; for each of a plurality of orthogonal wavefront modes of the wavefront modifying device: controlling the wavefront modifying device to vary a magnitude of the orthogonal wavefront mode over a predetermined number of magnitude settings; acquiring a series of readings of the detecting device, each reading corresponding to one of the magnitude settings; determining a quality metric value indicative of an information content of the reading for each reading in the series of readings, resulting in a series of quality metric values; and determining a reference parameter set for the wavefront modifying device corresponding to an optimum quality metric value based on the series of quality metric values.

An "adaptive optics system" is an optical system with adaptive capability for compensating for static and/or non-static optical aberrations introduced by the medium between an object and a detecting device. Adaptive optics systems are used for improved detection in such diverse fields as ophtalmology, astronomy, microscopy, and optical communication. The "object", obviously, may be different depending on field of application. In the case of ophtalmology, the "object" may, for example, be the retina. In astronomy applications, the "object" may, for example, be a star or a nebula. In optical communication, the "object" may, for example, be a transmitter telescope. In order to provide for the adaptive compensation of non-static optical aberrations, adaptive optics systems include a wavefront sensor for providing information about the (time-varying) spatial phase distribution of the light incident on the wavefront sensor and a wavefront modifying device for modifying the spatial phase distribution of the light based on signals from the wavefront sensor. After having been modified by the wavefront modifying device, the light from the object is directed towards a detecting device.

In the context of the present application, the term "wavefront modifying device" should be understood to mean any device that is controllable to modify the wavefront (spatial phase distribution) of light incident on the wavefront modifying device. Examples of such wavefront modifying devices include, for example, deformable mirrors, optically addressed spatial light modulators, electrically addressed spatial light modulators, etc.

The "detecting device" may be any device capable of detecting one or several properties of the light from the object. Such properties may, for example, include maximum intensity, intensity distribution, wavelength distribution, phase distribution etc. Examples of suitable detecting devices include a photodiode and an imaging device, such as a camera.

The spatial phase distribution (the shape of the wavefront) may be expressed in terms of a sum of "wavefront modes" with different coefficients/weights. In analogy, the wavefront modification of a wavefront modifying device (such as the shape of a deformable mirror) may also be expressed in terms of a sum of wavefront modes. Examples of orthogonal wavefront modes include so-called Zernike modes, but wavefronts/wavefront modifications may be expressed using several other kinds of orthogonal wavefront modes such as, for example, Legendre polynomials or Karhunen-Loève polynomials.

Furthermore, the "information content" of a reading of the detecting device is a property that indicates how close to aberration-free the acquired reading is. This property will depend on the reference beam used and the type of detecting device. For example, an acquired image that closely resembles a reference image has a higher information content than an acquired image that differs significantly from the reference image. In simpler embodiments a high acquired intensity may be determined to have a higher information content than a lower acquired intensity. Similarly, the higher the contrast of an image or detector reading, the higher the information content is. In optical communication applications, the information content can be said to be represented by the signal-to-noise ratio.

The present invention is based on the realization that an improved reference calibration can conveniently be achieved by performing a "partial calibration" for each of a plurality of orthogonal wavefront modes of the wavefront modifying device and, for each of these "partial calibrations", optimizing the information content obtained at the detecting device.

Since the method according to the present invention uses readings at the detecting device, rather than at the wavefront detector, aberrations along the detecting path are also calibrated for. This provides for an improved reference calibration.

According to various embodiments of the present invention the adaptive optics system may be configured such that it includes: a common path between the object and a beam splitting device, the common path including the at least one controllable wavefront modifying device; a detecting path between the beam splitting device and the detecting device; and a sensing path between the beam splitting device and the wavefront sensor. Signals from the wavefront sensor may be used to control the wavefront modifying device.

In embodiments including a beam splitting device, the "beam splitting device" may be any device capable of connecting the common path to the detecting path and to the sensing path. The routing provided by the beam splitting device may be static or dynamic. Static routing may, for example, be provided by a beam splitting device, such as a beam splitter. Dynamic routing may be achieved by a controllable beam deflection device, such as a mirror or other suitable optical element, or an optical switch. In the case of dynamic routing, a light beam incident on the beam splitting device from the common path may be controlled to alternatingly follow the detecting path and the sensing path.

According to various embodiments of the present invention, the orthogonal wavefront modes may be determined based on an interaction matrix defining a relation between different wavefront modifying states of the controllable wavefront modifying device and corresponding signals from the wavefront sensor.

Hereby, the result of the relative calibration (the relation between different settings of the wavefront modifying device and corresponding response signals from the wavefront sensor) can be re-used for the reference calibration, which facilitates the reference calibration.

Moreover, the orthogonal wavefront modes may be determined using singular value decomposition of the interaction matrix, which further facilitates the reference calibration, since it is a straightforward modal decomposition of the adaptive optics system without further approximation.

Furthermore, the method according to the above embodiments of the invention may further comprise the steps of controlling the wavefront modifying device to a plurality of different wavefront modifying states; registering, for each of the wavefront modifying states, a corresponding signal from the wavefront sensor; and determining the interaction matrix based on the plurality of different wavefront modifying states and the corresponding signals from the wavefront sensor.

According to the present invention, a reference parameter set is determined for each wavefront mode. By applying the reference parameter set of a particular mode before optimizing the quality metric value for the next wavefront mode, it has been empirically established that fewer iterations are generally required to arrive at a satisfactory reference setting for the adaptive optics system. Alternatively, the reference parameter set for each wavefront mode may be stored in memory and the reference setting may be determined based on the reference parameter sets stored in the memory. In this case, the reference setting may be determined to be a suitable combination of the reference parameter sets.

According to various embodiments of the method according to the present invention, the step of determining the reference parameter set may comprise the step of fitting the series of quality metric values to a predetermined function having a maximum or minimum corresponding to a minimum aberration of the wavefront mode.

This predetermined function may vary depending on the type of reference beam used. For a reference beam originating from a point source, for example, the predetermined function may be a Gaussian function or a quadratic function.

Although the method according to various embodiments of the present invention is applicable for readings from various detecting devices capable of detecting intensity variations in the light impinging on the detecting device, the detecting device may advantageously be an imaging device and the readings of the detecting device may be images.

In embodiments where the detecting device is an imaging device, such as a CCD-sensor or a CMOS-sensor, the step of determining quality metric values may comprise the step of transforming each image in the series of images from a spatial domain to a Fourier domain, which will maximize the information content and improve the precision in the determination of the quality metric values.

In the case when the imaging device comprises an image sensor having a plurality of pixels, the step of determining quality metric values may advantageously further comprise the step of summing a product of the Fourier transform of the image intensity and a measure indicative of a distance from the position of maximum intensity for each pixel in of the image sensor.

As mentioned above, the source of the reference beam may be a point source. In such embodiments, each of the quality metric values may advantageously be indicative of a Strehl ratio of an associated reading of the detecting device.

According to a second aspect of the present invention, the above-mentioned and other objects are achieved through an adaptive optics system for providing aberration compensated detection of light from an object, the adaptive optics system comprising: a detecting device for detecting light from an object; a wavefront sensor configured to provide signals indicative of a spatial phase distribution of light incident on the wavefront sensor; at least one controllable wavefront modifying device arranged such that light from said object passes via said wavefront modifying device to said detecting device and to said wavefront sensor; a control system connected to the wavefront sensor and to the wavefront modifying device, said control system being operable in a calibration mode and in a regulation mode, wherein said control system comprises: an output for providing control signals to the wavefront modifying device; a first input for receiving signals from the wavefront sensor; a second input for receiving readings the detecting device; a wavefront modifying device controller for controlling the wavefront modifying device; calibration circuitry for determining calibration parameters for the adaptive optics system; and a memory for storing said calibration parameters, wherein: when the control system operates in the calibration mode: the wavefront modifying device controller, for each of a plurality of orthogonal wavefront modes of the wavefront modifying device, controls the wavefront modifying device to vary a magnitude of the orthogonal wavefront mode over a predetermined number of magnitude settings; and the calibration circuitry, for each of the plurality of orthogonal wavefront modes, determines a quality metric value indicative of an information content of each reading in a series of readings received from the detecting device, each reading corresponding to one of the magnitude settings, resulting in a series of quality metric values; determines a reference parameter set for the wavefront modifying device corresponding to an optimum quality metric value based on the series of quality metric values for each of the plurality of orthogonal wavefront modes; and when the control system operates in the regulation mode: the wavefront modifying device controller regulates the wavefront modifying device based on signals from the wavefront sensors and the reference parameter set.

The various parts of the control system comprised in the adaptive optics system may be embodied as separate components and/or as software in one or several microprocessor(s).

Further embodiments and effects of this second aspect of the present invention are largely analogous to those described above with reference to the first aspect of the invention.

BRIEF DESCRIPTION OF THE DRAWINGS

These and other aspects of the present invention will now be described in more detail, with reference to the appended drawings showing at least one example embodiment of the invention, wherein:

FIG. 1b is a schematic block diagram of the control system comprised in the adaptive optics system in FIG. 1a.

DETAILED DESCRIPTION OF AN EXAMPLE EMBODIMENT OF THE INVENTION

In the below detailed description, example embodiments of the present invention are mainly described with reference to an adaptive optics system where a point source is used to generate the reference beam and the detecting device is provided in the form of an image sensor which is used to acquire pixelated images of the point source. Furthermore, so-called guide stars are described as being generated by the adaptive optics system.

This should by no means be construed as limiting the scope of the present invention, which also encompasses cases when other types of reference beams are used, which result in another spatial intensity distribution at the plane of the detecting device. For example, such reference beams may provide an edge or a checkered pattern at the detecting device. Furthermore, the detecting device need not be an imaging device, but may be a non-imaging detector, such as a photo diode or equivalent. Moreover, one or several externally provided guide stars may be used. In astronomy-related applications, for example, one or several stars may be used as guide stars.

Figure 1A:
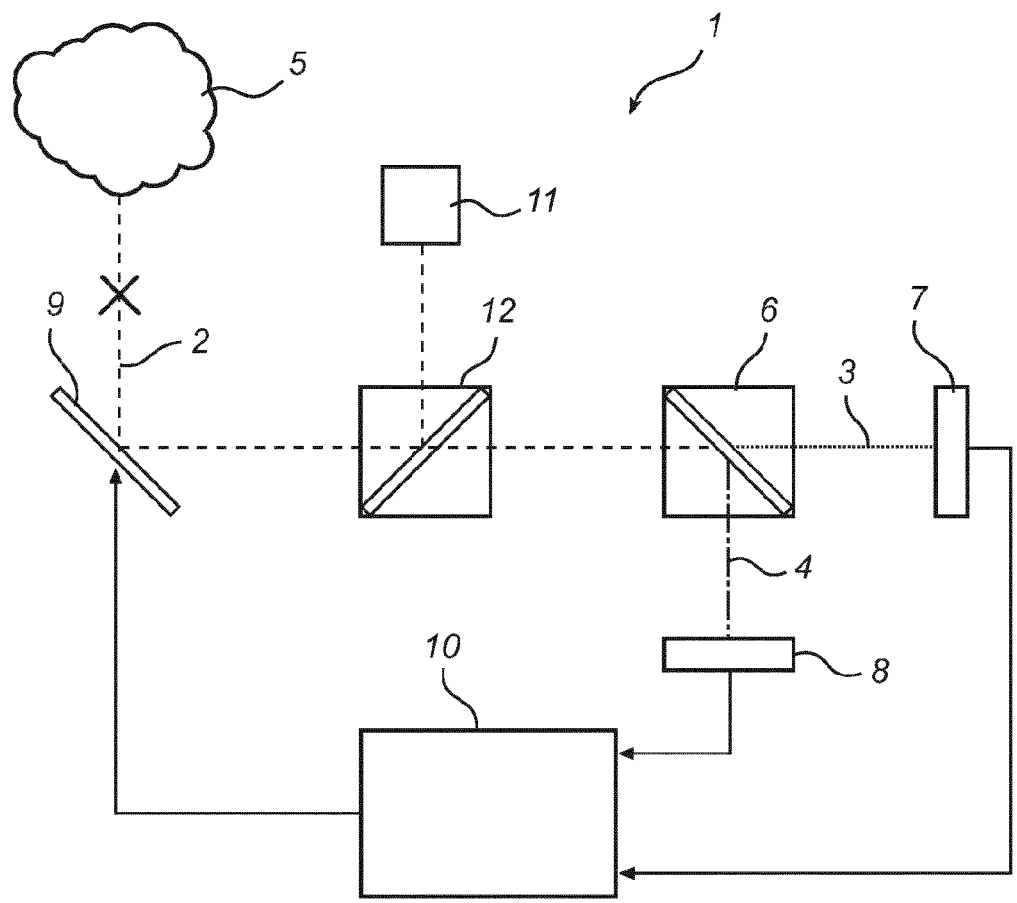
FIG. 1a schematically shows an adaptive optics system according to an exemplary embodiment of the present invention.

FIG. 1a schematically shows an exemplary adaptive optics system 1 according to an embodiment of the present invention. The adaptive optics system 1 in FIG. 1a comprises a common path 2, a sensing path 3, and a detecting path 4. In FIG. 1a, the common path 2 is indicated by a dashed line, the sensing path 3 is indicated by a dotted line, and the detecting path 4 is indicated by a dashed-dotted line. The common path 2 is the optical path between the object 5 and a beam splitting device 6, here in the form of a cold mirror, the sensing path 3 is the optical path between the beam splitting device 6 and a wavefront sensor 7, and the detecting path 4 is the optical path between the beam splitting device 6 and a detecting device 8. The adaptive optics system 1 in FIG. 1a further comprises a controllable wavefront modifying device 9 arranged in the common path, and a control system 10 that is connected to the wavefront modifying device 9, to the wavefront sensor 7, and to the detecting device 8. In addition, the adaptive optics system 1 in FIG. 1a comprises a guide star light-source 11 and a second beam splitting device 12, here in the form of a wedge beam splitter. The beam splitting device 12 redirects one light beam to follow the common path 2 to the object 5, where the light-beam provides a so-called guide star, or multiple light beams to follow the common path 2 to the object 5, where the light beams provide multiple guide stars.

When in operation, the adaptive optics system 1 in FIG. 1a corrects for time-varying aberrations between the object 5 and the wavefront sensor 7 by regulating the wavefront modifying device 9 based on the known position(s) of the guide star(s). For this correction to work, there needs to be a known relation between different states of the wavefront modifying device 9 and corresponding readings of the wavefront sensor 7. To achieve this relation, the adaptive optics system 1 needs to be calibrated.

Calibration is accomplished by imaging one point source or multiple point sources, via the wavefront modifying device 9, on the wavefront sensor 7. The position of the point source(s) will vary depending on the application field of the adaptive optics system 1 (retinal imaging, astronomy, etc). According to an embodiment of the present invention, one exemplary position for the point source(s) (which may be a reflection of the point source(s) formed by the guide star light-source 11) is at a suitable position on the common path 2 between the object 5 and the controllable wavefront-modifying device 9, designated by "X" in FIG. 1a.

With the point source(s) in place at the position denoted by "X", the wavefront modifying device 9 is controlled by the controller between different wavefront modifying states, and corresponding signals from the wavefront sensor 7 are registered. Based on the different wavefront modifying states and the corresponding signals from the wavefront sensor 7, a so-called interaction matrix is determined that can be used to correlate between changes at the wavefront modifying device 9 and corresponding changes in the signal from the wavefront sensor 7.

The above-described calibration is a relative calibration in the meaning that differences between states of the wavefront modifying device 9 are correlated to differences between corresponding signals from the wavefront sensor 7. For many types of wavefront sensors 7, a reference calibration or zero-point calibration is additionally required. Such a reference calibration is provided through the various embodiments of the present invention.

When performing a reference calibration according to various embodiments of the present invention, a reference light-source (not shown in FIG. 1a) is inserted at a suitable position on the common path 2 between the object 5 and the controllable wavefront-modifying device 9. An advantageous choice of position may be the same exemplary position "X" designated for the point source(s) in the above-mentioned relative calibration.

It should be noted that the adaptive optics system 1 described above with reference to FIG. 1a is a simplified system, which only includes the key components of an adaptive optics system. In reality, as is well known to those skilled in the art, an adaptive optics system includes, depending on the field of application, various additional optics for shaping the various light-beams and for providing for adjustability and tuning of the adaptive optics system. A more detailed description of an adaptive optics system for which the reference calibration according to various embodiments of the present invention would be suitable is provided by U.S. Pat. No. 7,639,369, which is hereby incorporated by reference in its entirety.

As was touched upon above, the adaptive optics system 1 in FIG. 1a is controllable to operate at least in a calibration mode and in a regulation mode. In each of these states, the various parts of the adaptive optics system 1 are controlled by the control system 10, which will be described in more detail below with reference to the schematic block diagram in FIG. 1b.

Figure 1B:
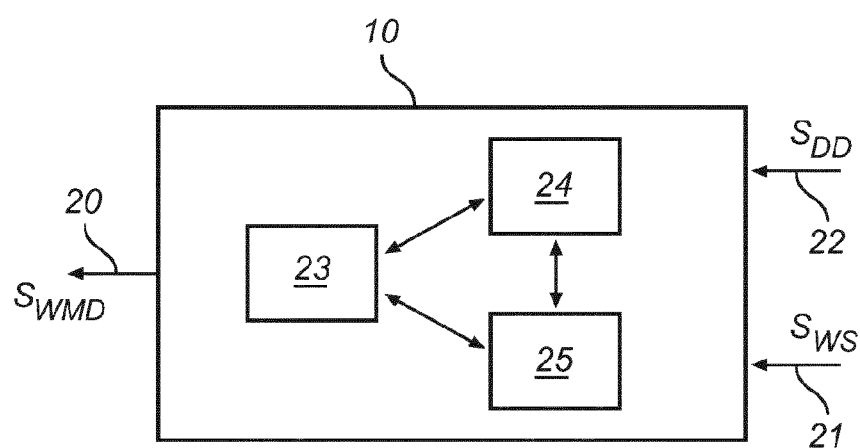

With reference to FIG. 1b, the control system 10 comprises an output 20 for providing control signals $S_{WMD}$ to the wavefront modifying device 9, a first input 21 for receiving signals $S_{WS}$ from the wavefront sensor 7, and a second input 22 for receiving signals $S_{DD}$ from the detecting device 8. As is schematically indicated in FIG. 1b, the control system 10 further comprises a wavefront modifying device controller 23 for controlling the wavefront modifying device 9, calibration circuitry 24 for determining calibration parameters for the adaptive optics system 1, and a memory 25 for storing the calibration parameters.

In the regulation mode, the wavefront modifying device controller 23 controls the wavefront modifying device 9 based on signals from the wavefront sensor 7, and the calibration parameters stored in the memory 25. The purpose of the regulation is to control the wavefront modifying device 9 to keep the wavefront associated with the guide-star(s) constant at the wavefront sensor 7 and thereby continuously compensate for variations in the optical properties between the object 5 and the wavefront sensor 7.

The calibration parameters stored in the memory 25 are crucial to the ability of the adaptive optics system 1 to accurately perform the above-mentioned regulation. The calibration parameters are therefore advantageously determined based on both a relative calibration as briefly described above and a reference calibration. In the following, a reference calibration method according to an exemplary embodiment of the present invention will be described with reference to the flow chart in FIG. 2, as well as with continued reference to FIGS. 1a-b.

In the first step 100, a reference light-source is arranged on the common path 2, for example at the position denoted "X" in FIG. 1a.

Figure 2:
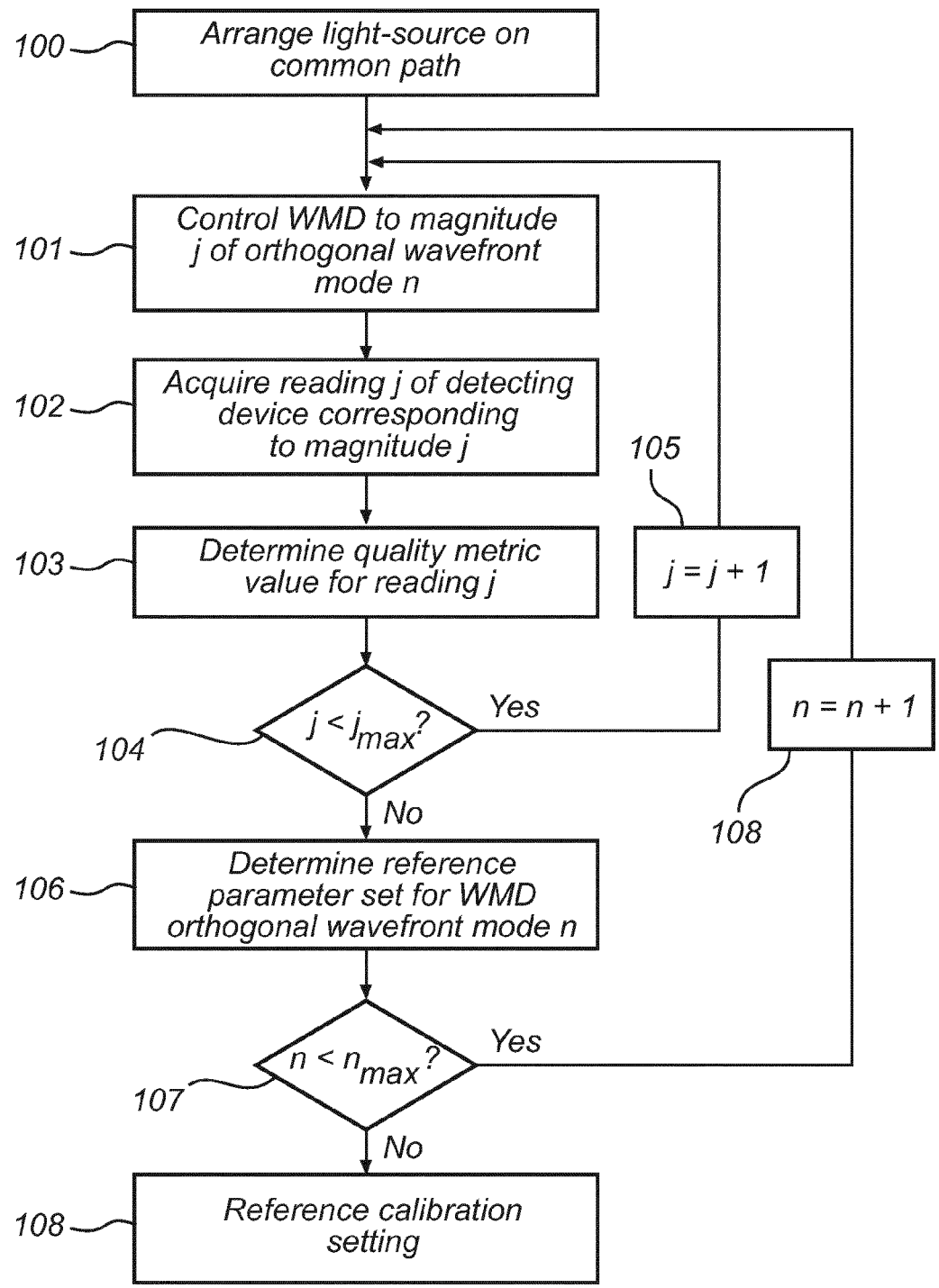
FIG. 2 is a schematic flow chart of a method according to an embodiment of the present invention.

For each of a number of orthogonal wavefront modes, the wavefront modifying device 9 is then controlled to vary the magnitude of the orthogonal wavefront mode over a number of magnitude settings. In FIG. 2, this is illustrated as a double loop where a number of steps are performed for each magnitude setting j for a given orthogonal wavefront mode n, and a number of steps are performed for each orthogonal wavefront mode n once the steps of all magnitude settings j have been carried out.

In FIG. 2, the steps performed for each magnitude setting j are denoted 101-105. In step 101, orthogonal wavefront mode n of the wavefront modifying device 9 is controlled to magnitude j by the wavefront modifying device controller 23. Subsequently, in step 102, a reading j of the detecting device 8 corresponding to magnitude setting j is acquired through the second input 22 of the control system 10. Thereafter, in step 103, a quality metric value is determined by the calibration circuitry 24. The quality metric value is indicative of the information content of reading j and may for example indicate a deviation between a known properties of the reference light beam and the properties of the reference light beam detected by the detecting device 8. When steps 101-103 have been carried out for magnitude setting j, it is checked in step 104 if all magnitude settings have been stepped through, that is if $j=j_{max}$. If this is not the case, the magnitude setting counter is incremented by 1 in step 105, and steps 101-104 are repeated. If $j=j_{max}$, the method proceeds to step 106, in which the calibration circuitry 24 determines a reference parameter set for the wavefront modifying device 9 corresponding to an optimum quality metric value for the current orthogonal wavefront mode n based on the quality metric values determined for the different magnitude settings j. This determination of reference parameter set may advantageously be performed through a curve fit of the pairs of magnitude settings and corresponding quality metric values to a predefined function.

After having determined the reference parameter set for orthogonal wavefront mode n, it is checked in step 107 if all orthogonal wavefront modes have been stepped through, that is if $n=n_{max}$. If this is not the case, the orthogonal wavefront mode counter is incremented by 1 in step 108, and steps 101-107 are repeated. Before returning to step 101, the orthogonal wavefront modes that have already been cycled through may be set according to their determined reference parameter sets. It has been empirically established that this generally results in a faster calibration than if the other orthogonal wavefront modes (other than orthogonal wavefront mode n) are controlled to a predefined setting during the magnitude variation of orthogonal wavefront mode n.

If $n=n_{max}$, the method proceeds to step 108 and provides a reference calibration setting for the adaptive optics system 1 based on the reference parameter sets for the orthogonal wavefront modes.

EXAMPLE

Theoretical Discussion and Experimental Setup

Theoretical Discussion

Quality metrics for general objects have been considered, but given the fact that the interaction matrix of most adaptive optics systems is calibrated with a point source, the discussion here will be limited to that. Image plane quality metrics can then be encircled energy radius, $I^n(x)$ where $I(x)$ is the focal plane intensity etc. A commonly used metric that describes the performance of an adaptive optics system is the Strehl ratio:

$$S = I(0,0)/I_*(0,0) = \int \tilde{I}(f)df / \int \tilde{I}_*(f)df \approx \exp(-\sigma_\Phi^2) \quad (1)$$

where $I(0,0)$ is the on-axis image intensity, $I_*(0,0)$ is the on-axis aberration-free image intensity in the focal plane and ~ denotes the Fourier transform. The second equality is a consequence of the definite integral theorem, and following that, the Marèchal approximation is given, valid for phase deviations conforming to Gaussian statistics. The Marèchal approximation is seen to describe a Gaussian function of the RMS pupil phase error $\sigma_\Phi$, but is also commonly given in a quadratic form $S \approx 1-\sigma_\Phi^2$. Both approximations are valid for $\sigma_\Phi \ll 1$. Looking at simulated Strehl values for the Zernike modes from 2nd to 5th radial order, it is seen that the Strehl value will approximate a Gaussian function $\exp(-\sigma_\Phi^2)$ over a larger aberration interval than the quadratic decay $1-\sigma_\Phi^2$. If the actual tip-tilt contribution is neglected, which does not affect the image quality, the peak intensity is found at $x_{max} = \arg\max_x I(x)$ and according to the shift theorem it is found that $$S_\perp = I(x_{max})/I_*(0,0) = \int \tilde{I}(f)\exp(i2\pi f x_{max})df / \int \tilde{I}_*(f)df \approx \exp(-\sigma_{\Phi_\perp}^2) \quad (2)$$

It is obvious from this expression that minimizing the phase error (the purpose of an adaptive optics system) is identical to maximizing the numerators. In the discrete 21st century, an image sampled at or near the Nyquist-limit will suffer from severe discretization implying that the spatial domain has been found less suitable for the task of estimating the Strehl value. In case it is used, it is common to change the sampling interval by zero-padding in the Fourier domain followed by inverse transformation. Since all information is contained within the Fourier domain, the quality metric used here is based on the Fourier transformed image. For a discrete image $I_{rs}$ from the CCD/CMOS detector, where the pixel coordinates are given by the positive integers r and s, the sub-pixel shift in the image domain ($x_{max}$, $y_{max}$) is estimated with a quadratic interpolation around the maximum pixel intensity value at $I_{r_{max} s_{max}}$ giving:

$$y_{max} = (r_{max} - m/2 - 1) + \frac{I_{(r_{max}-1)s_{max}} - I_{(r_{max}+1)s_{max}}}{2[I_{(r_{max}-1)s_{max}} + I_{(r_{max}+1)s_{max}} - 2I_{r_{max}s_{max}}]}, \quad (3)$$

and analogous for $x_{max}$. The continuous pixel coordinates x and y have an origin in the center if the discrete image, hence the subtraction of $m/2+1$ as the image format is m×m. The quality metric value according to this exemplary embodiment of the invention is then given by the discrete version of the Fourier domain numerator in Eq. (2)

$$Q = \Sigma_{r=1}^m \Sigma_{s=1}^m \tilde{I}_{rs} \exp(i2\pi[(r-m/2-1)y_{max} + (s-m/2-1)x_{max}]/m). \quad (4)$$

It is seen that maximizing this quality metric value will minimize the wavefront error and maximize the Strehl ratio.

$\tilde{I}_{rs}$ is the discrete Fourier transform (e.g. using FFT) of the point source image $I_{rs}$. Since the image intensity is a real function, its Fourier transform will be Hermitian, i.e., $\tilde{I}(-f) = \tilde{I}^*(f)$, and the imaginary part will cancel out to give a real quality metric value. Hence the summation can be limited to the real part in half of the Fourier domain, to speed up the calculations of the quality metric value.

The phase imposed in a pupil plane by an exemplary waveform modifying device in the form of a deformable mirror with k actuators can be described by $$\Phi(\xi) = \Sigma_k c_k \Phi_k^I(\xi) \quad (5)$$

where $\Phi_k^I(\xi)$ is the point response function, or influence function, of a unit actuator command $c_k = 1$. The phase is measured by the wavefront sensor producing the measurement vector s. During reference calibration of an adaptive optics system, the interaction matrix $s = Gc$ is obtained by measuring the impulse response of each actuator and collecting these wavefront sensor measurements as columns in G. During closed loop (in the regulation mode) the (truncated) pseudoinverse is used to update the shape of the deformable mirror $c = G_+s$, and common in the control of adaptive optics systems is to obtain the singular value decomposition $G = V\Lambda U^T$. The columns of V and U, $v_m$ and $u_n$, are the left and right singular modes defining orthonormal vectors in sensor measurement space and actuator command space respectively. These are also ordered according to sensitivity, starting with the most sensitive modes. Hence each singular mode is an orthogonal phase distribution according to Eq. (5), i.e.

$$\Phi_n(\xi) = \Sigma_k U_{kn} \Phi_k^I(\xi) \quad (6)$$

and changing the magnitude of this phase mode to $\alpha_n \Phi_n(\xi)$ corresponds to applying the actuator commands $\alpha_n u_n$. It is certainly common to use also other orthogonal expansions, e.g. Zernike polynomials, to describe the phase, but the SVD method offers to a natural decomposition of the adaptive optics system's inputs and outputs without any further approximations, simultaneously grading the sensitivity of the singular modes. The exemplary method presented here exploits scanning of the orthogonal singular modes $\Phi_n(\xi)$. According to Eqs. (1-4) the quality metric value Q will follow a Gaussian function for small aberrations. Hence, for each scanned singular mode (changing $\alpha_n$ over j points) a least squares fit gives:

$$\begin{bmatrix} \hat{a}_n \\ \hat{b}_n \\ \hat{k}_n \end{bmatrix} = \arg\min_{a_n, b_n, k_n} \sum_{j=1}^{j_{max}} \left\| Q_j - k_n \exp\left(-\frac{(\alpha_{n,j} - \alpha_n)^2}{b_n^2}\right) \right\|^2 \quad (7)$$

where the last term in the squared norm defines a Gaussian function, given by the parameters $\alpha_n$, $b_n$ and $k_n$. The peak of the estimated function is found at $\hat{\alpha}_n$, and hence for a specific singular mode, the Strehl is maximized and the wavefront error is minimized for $\hat{\alpha}_n \Phi_n(\xi)$ As all singular modes have been optimized, the mirror shape that optimizes the performance of the adaptive optics system will be $c_* = \Sigma_n \hat{\alpha}_n u_n$. An advantage of this exemplary embodiment of the method according to the present invention is that all parameters that are needed to achieve the optimization are already available in most adaptive optics systems, and it can be executed immediately after the interaction matrix has been calibrated without any alteration of the setup, but simply with the provision of a reference light-source. No further assumptions need to be made, nor is any additional equipment or alteration of the optical system needed.

There are of course limitations on the possible level of correction for the method. Due to the orthogonality of the singular modes, the method will not converge to a local maximum. However, for the case of severe initial aberrations (no core in the point spread function) several iterations of the method may be required. For the practical implementation of the correction procedure, when a new calibration is needed we have found it useful to start the new calibration from the preceding calibration of the wavefront modifying device, i.e. from the old command vector $c_*$, since the quasi-static aberrations in the imaging path are likely similar. Likewise, the first 10 modes may advantageously be scanned twice, since loss of alignment and thermally induced errors will plausibly introduce low-order aberrations such as astigmatism and coma, and these are commonly present among the well-sensed modes of the adaptive optics system.

Experimental Setup

The exemplary method presented above has been implemented in an ophthalmic adaptive optics instrument such as that described in U.S. Pat. No. 7,639,369. A single mode optical fiber has been used as a point source ($\lambda$=635 nm) on the common path, and the point spread function has been optimized according to the method given above. The sampling of the CCD detector corresponds to Nyquist sampling. The scan interval of each mode was adjusted individually, with an increasing interval of $\alpha_n$ for each mode, roughly corresponding to $\sigma_\Phi \approx [-0.15, 0.15]$ waves. Likewise, the number of modes $n_{max}$ to optimize was limited since it was obvious that that ill-sensed modes did not follow the Maréchal approximation, and the threshold was set according to this criterion. The first 10 modes were optimized twice, since most of the energy is likely contained within these modes. The number of scan points was $j_{max}$=10.

The peak intensity position of the resulting point spread function has been estimated according to Eq. (3), applying this phase shift to the Fourier transformed image according to Eq. (2), which then generates the centred point spread function through an inverse Fourier transform. The intensity of the central pixel was then compared to the ideal point spread function, where the energy in both point spread functions were adjusted to the same level.

The invention claimed is:

1. A method of determining a reference calibration setting for an adaptive optics system comprising:
    a detecting device for detecting light from an object; and
    at least one controllable wavefront modifying device arranged such that light from said object passes via said wavefront modifying device to said detecting device, said method comprising the steps of:
    arranging a light-source between said object and said wavefront modifying device to provide a reference light beam to the detecting device via the wavefront modifying device;
    for each of a plurality of orthogonal wavefront modes of the wavefront modifying device:
        controlling the wavefront modifying device to vary a magnitude of the orthogonal wavefront mode over a predetermined number of magnitude settings;
        acquiring a series of readings of the detecting device, each reading corresponding to one of said magnitude settings;
        determining a quality metric value indicative of an information content of the reading for each reading in said series of readings, resulting in a series of quality metric values; and
    determining a reference parameter set for the wavefront modifying device corresponding to an optimum quality metric value based on the series of quality metric values.

2. The method according to claim 1, wherein said adaptive optics system further comprises a wavefront sensor arranged such that light from said object passes to said wavefront sensor via said wavefront modifying device,
    said wavefront sensor being configured to provide signals indicative of a spatial phase distribution of light incident on the wavefront sensor, and
    wherein said orthogonal wavefront modes are determined based on an interaction matrix defining a relation between different wavefront modifying states of the controllable wavefront modifying device and corresponding signals from the wavefront sensor.

3. The method according to claim 2, wherein said orthogonal wavefront modes are determined using singular value decomposition of the interaction matrix.

4. The method according to claim 2, further comprising the steps of:
    controlling the wavefront modifying device to a plurality of different wavefront modifying states;
    registering, for each of said wavefront modifying states, a corresponding signal from the wavefront sensor; and
    determining said interaction matrix based on said plurality of different wavefront modifying states and said corresponding signals from the wavefront sensor.

5. The method according to claim 1, further comprising the step of, for each of said plurality of wavefront modes:
    controlling the wavefront modifying device using said reference parameter set.

6. The method according to claim 1, wherein said step of determining said reference parameter set comprises the step of:
    fitting said series of quality metric values to a predetermined function having a maximum or a minimum corresponding to a minimum aberration of the wavefront mode.

7. The method according to claim 1, wherein said detecting device is an imaging device, and each of said readings of the detecting device is an image.

8. The method according to claim 7, wherein said step of determining quality metric values comprises the step of:
    transforming each image in said series of images from a spatial domain to a Fourier domain.

9. The method according to claim 8, wherein said imaging device comprises an image sensor having a plurality of pixels,
    said step of determining quality metric values further comprising the step of:
    summing a product of the Fourier transform of the image intensity and a measure indicative of a distance from the position of maximum intensity for each pixel in of the image sensor.

10. The method according to claim 1, wherein said light-source is a point source and each of said quality metric values is indicative of a Strehl ratio of an associated reading of the detecting device.

* * * * *

UNITED STATES PATENT AND TRADEMARK OFFICE
CERTIFICATE OF CORRECTION

PATENT NO. : 9,733,474 B2
APPLICATION NO. : 15/142238
DATED : August 15, 2017
INVENTOR(S) : Per Knutsson Page 1 of 1

It is certified that error appears in the above-identified patent and that said Letters Patent is hereby corrected as shown below:

On the Title Page

Item (63) Related U.S. Application Data should read:
Continuation of application No. 14/349,093, filed on Apr. 2, 2014, now Pat. No. 9,335,603, which is a 371 of PCT/EP2012/069620 filed Oct. 4, 2012.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*